(12) United States Patent
Ivinson et al.

(10) Patent No.: US 9,346,155 B2
(45) Date of Patent: May 24, 2016

(54) END ALIGNED FLEXIBLE CONNECTION SLEEVES

(71) Applicants: David Ivinson, Camarillo, CA (US); John Nino, Simi Valley, CA (US)

(72) Inventors: David Ivinson, Camarillo, CA (US); John Nino, Simi Valley, CA (US)

(73) Assignee: ECA Medical Instruments, Newbury Park, CA (US)

( * ) Notice: Subject to any disclaimer, the term of this patent is extended or adjusted under 35 U.S.C. 154(b) by 221 days.

(21) Appl. No.: 14/079,411

(22) Filed: Nov. 13, 2013

(65) Prior Publication Data
US 2014/0070498 A1 Mar. 13, 2014

Related U.S. Application Data

(63) Continuation of application No. PCT/US2012/033339, filed on Apr. 12, 2012.

(60) Provisional application No. 61/886,272, filed on Oct. 3, 2013, provisional application No. 61/486,727, filed on May 16, 2011.

(51) Int. Cl.
*B25B 23/00* (2006.01)
*B23B 31/107* (2006.01)

(52) U.S. Cl.
CPC ......... *B25B 23/0035* (2013.01); *B23B 31/1071* (2013.01); *Y10T 29/4987* (2015.01); *Y10T 29/49826* (2015.01); *Y10T 29/49853* (2015.01); *Y10T 29/49876* (2015.01); *Y10T 29/49945* (2015.01); *Y10T 29/53657* (2015.01); *Y10T 29/53843* (2015.01); *Y10T 29/53909* (2015.01); *Y10T 279/17162* (2015.01)

(58) Field of Classification Search
CPC ............ B25B 23/0035; B23B 31/1071; Y10T 29/53909; Y10T 29/53843; Y10T 29/49945; Y10T 29/49876; Y10T 29/53657; Y10T 29/4987; Y10T 29/49853; Y10T 29/49826; Y10T 279/17162
See application file for complete search history.

(56) References Cited

U.S. PATENT DOCUMENTS

| 2,807,473 | A | 9/1957 | Kiehne |
| 4,453,449 | A | 6/1984 | Hollmann |
| 5,490,683 | A | 2/1996 | Mickel |
| 7,810,817 | B1 | 10/2010 | Gao |

OTHER PUBLICATIONS

International Search Report dated Nov. 14, 2012, issued in PCT/US2012/033339.

*Primary Examiner* — John C Hong
(74) *Attorney, Agent, or Firm* — Baker & Hostetler LLP

(57) ABSTRACT

A latch and catch arrangement is disclosed, whereby a sleeve supporting a flexible hinge is oriented over a bearing in guide. An asymmetrical alignment via a latch and catch between the sleeve and tool collar orients a flexible hinge, which may be of reduced thickness, over a bearing in a guide. The bearing moves upward when a tool is inserted into a tool socket, and the flexible hinge, properly oriented by the alignment catch/latch, keeps the bearing in the tool socket while allowing necessary movement to insert and remove a tool.

21 Claims, 16 Drawing Sheets

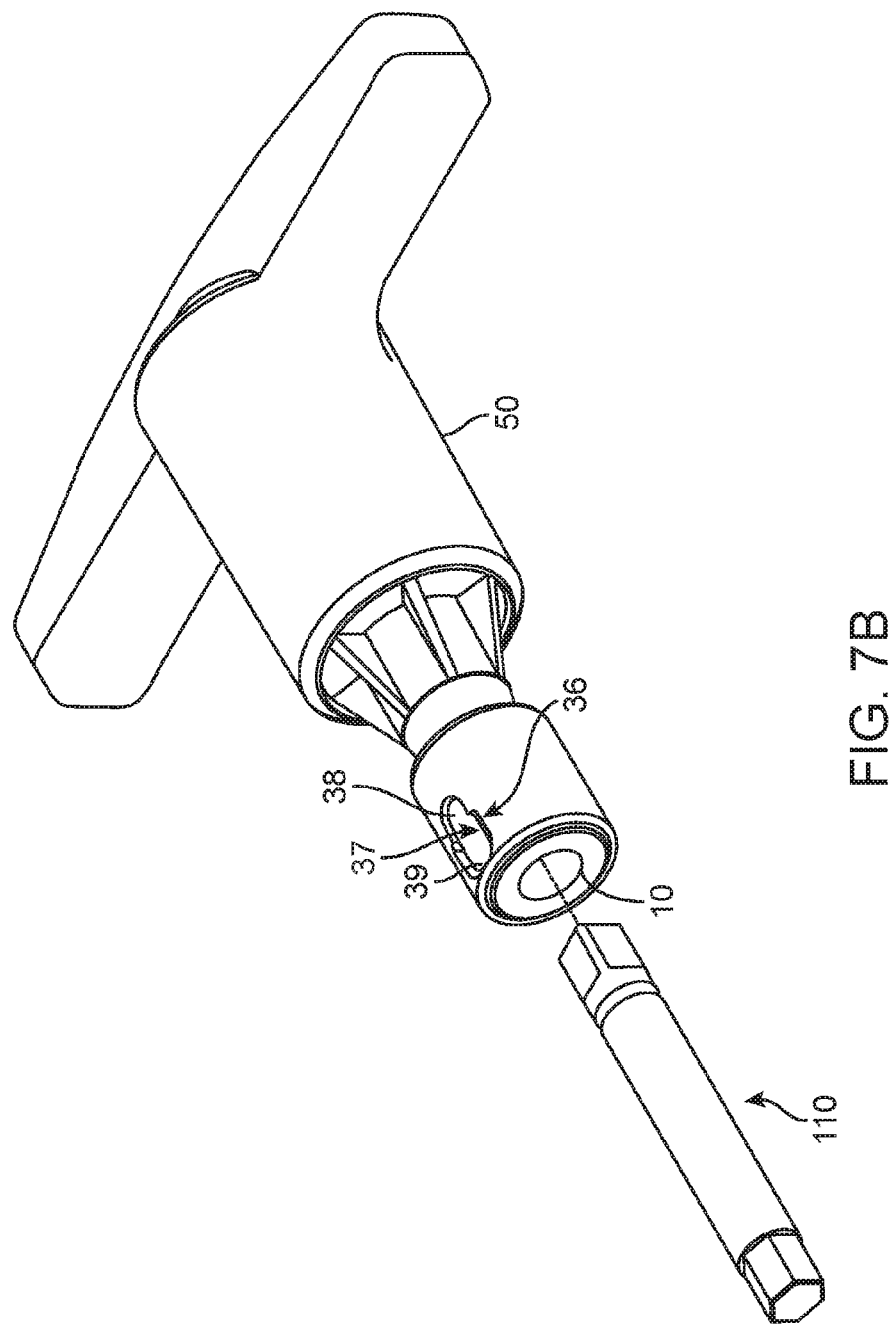

END ALIGNED FLEXIBLE CONNECTION SLEEVES

CROSS-REFERENCE TO RELATED APPLICATIONS

This application claims the full Paris Convention benefit of, and priority to, U.S. provisional application 61/486,727 filed May 18, 2011, international application no. PCT/US2012/033339 filed Apr. 12, 2012, and, U.S. provisional application 61/886,272 filed Oct. 3, 2013, the contents of which are incorporated by this reference as if fully set forth herein in their entirety.

BACKGROUND

1. Field

This disclosure relates to an end aligned flexible hinge connection device and system.

2. General Background

Handles with removable tools are known in the art. Friction fits, pressure fits and spring-loaded mounts are traditionally used.

A socket wrench is a type of wrench that uses separate, removable sockets to fit different sizes of nuts and bolts. A socket wrench is a wrench with interchangeable heads called sockets that attach to a fitting on the wrench, allowing it to turn different sized bolts and other fasteners. Commonly, a hand tool consists of a handle with a ratcheting mechanism built in, so it can be turned using a back-and-forth motion. A tool such as a socket snaps onto a fitting on the handle. The handle supplies the mechanical advantage to provide the torque to turn the socket. The advantage of a socket wrench is that, instead of a separate wrench for each of the many different bolt heads used in modern machinery, only a separate socket is needed, saving space.

SUMMARY

The disclosure teaches a flexible connector or living hinge for use in mounting tools to a larger element such as a handpiece, shaft or the like. In some instances the flexible living hinge is of a reduced thickness as compared to the surrounding sleeve.

In some exemplary implementations there are disclosed aspects of a method and device with a tool collar having a closed back end and an open front, having an outer annular wall providing an open end shaped surrounding a tool socket. Said tool socket also having an (inner) annular wall. A bearing guide is fluidly connected between both inner and outer annular walls. A bearing is fitted within the guide. To limit the bearing from falling through the bearing guide into the tool socket, the end of the bearing guide adjacent to the inner annular wall is of a smaller diameter than the bearing. To prohibit loss of the bearing and/or to dynamically move said bearing within said bearing guide, a sleeve with a flexible hinge (or living hinge) is placed or affixed over the outer annular wall of the tool collar. The flexible hinge having a thickness which is less than the sleeve it is formed with. In some implementations, a shaft may be affixed to the closed back end of the tool collar whereby said tool collar may be affixed to one of a handle, a larger device and a power tool.

In some exemplary implementations there are disclosed aspects of a method and device with a tool collar having a closed back end and an open front having; an outer annular wall provides an open end shaped surrounding a tool socket. Said tool socket also having an (inner) annular wall. A bearing guide is fluidly connected between both inner and outer annular walls. A bearing is fitted within the guide. To limit the bearing from falling through the bearing guide into the tool socket, the end of the bearing guide adjacent to the inner annular wall is of a smaller diameter than the bearing. To prohibit loss of the bearing and/or to dynamically move said bearing within said bearing guide, a sleeve with a flexible hinge formed therein is placed or affixed over the outer annular wall of the tool collar and an alignment guide is formed located at least at one of the front and back of the tool collar, to limit orientation of the flexible hinge. In some implementations, a shaft may be affixed to the closed back end of the tool collar whereby said tool collar may be affixed to one of a handle, a larger device and a power tool.

The disclosure teaches aspects of a flexible connector or living hinge for use in mounting tools to a larger element such as a handpiece, shaft or the like. Generally, a tool collar with a closed back end having a shaft formed as part of, or affixed thereto. Said tool collar comprises an outer annular wall having an open front having shaped into a tool socket. Said tool socket has an inner annular wall. A bearing guide is fluidly connected between both annular walls and a bearing may be fitted within said guide. To limit said bearing from falling through said bearing guide, the end of the bearing guide adjacent to the tool shaft is of a smaller diameter than the bearing therein. To prohibit loss of the bearing and/or to dynamically move said bearing within said bearing guide, a sleeve with a flexible hinge (or living hinge) is placed or affixed in a fixed position over said tool collar the shaft is affixed to one of a handle device and a power tool. The flexible hinge is oriented via one or more alignment guide (acting as a latch or catch) formed on at least one of the back end of the tool collar and the front of the tool collar whereby a corresponding latch or catch formed as part of the sleeve mates therewith. The flexible hinge may be the same or similar thickness as the sleeve (also referred to as a homogeneous) or non-homogeneous or variable thickness. In some instances, a tool is fitted into said tool socket. The tool provides a latch for said bearing. In such instances the bearing forms a catch. The latch may be an annular bearing guide such as a concave channel. The annular bearing guide may also be a cut out, divot, well, or the like and not circumnavigate the tool. In some instances, multiple flexible hinges formed in said sleeve and multiple bearings which fit into multiple annular bearing guides. In some instances of multiple bearings, the bearing guides of the tool collar are positioned generally aligned. In other instances, said bearing guides are disaligned. Said sleeve may be formed of at least one of plastics, resins, metals, composites, rubbers, and polymers.

The disclosure teaches methods of reversibly attaching tools wherein a tool collar with an open ended tool socket (for mounting a tool) has a movable bearing within a guide in fluid connection with the outer and inner walls of the tool collar. A sleeve material is fitted over the tool collar. The sleeve has at least a flexible region (also called a living hinge) which is seated in a predetermined alignment above the bearing in the guide. The flexible hinge region of the sleeve is displaceable by the pressure exerted thereon from the bearing moving against it as the bearing is displaced during insertion of a tool within the open ended tool socket. The flexible hinge may be the same or similar thickness as the sleeve (also referred to as a homogeneous) or non-homogeneous or variable thickness. When an annular bearing guide formed in said tool aligns with said bearing, the flexible hinge urges the bearing into the annular bearing guide, thereby cooperating in a latch and catch arrangement to hold the tool in the tool shaft.

The disclosure teaches methods of reversibly attaching tools wherein a tool collar with an open ended tool socket (for mounting a tool) has a movable bearing within a guide in fluid connection with the outer and inner walls of the tool collar. A sleeve material is fitted over the tool collar. The sleeve has at least a flexible region (also called a living hinge) which is seated in a predetermined alignment above the bearing in the guide. Alignment is via a cooperative latch/catch arrangement between portions of the sleeve and the tool collar. More specifically, at at least one of the back end and open front of the tool collar, there is positioned via an end centric alignment latch or catch. In some instances, the alignment latch or catch is formed at the back end of the tool socket. In other instances, it is formed at the front end of the tool socket. The corresponding latch or catch is formed on the corresponding end of the sleeve (front or back), thereby placing the flexible hinge in the pre-determined orientation. The alignment latch or catch may be asymmetrical. The flexible hinge region of the sleeve is displaceable by the pressure exerted thereon from the bearing moving against it as the bearing is displaced during insertion of a tool within the open ended tool socket. The flexible hinge may be the same or similar thickness as the sleeve (also referred to as a homogeneous) or non-homogeneous or variable thickness. When an annular bearing guide formed in said tool aligns with said bearing, the flexible hinge urges the bearing into the annular bearing guide, thereby cooperating in a latch and catch arrangement to hold the tool in the tool shaft.

The disclosure teaches a method of reversibly attaching tools, wherein a tool collar with an open ended tool socket having a movable bearing within a guide is in fluid connection with the outer and inner walls of said tool collar. A sleeve material is fitted over said tool collar. The sleeve has a partially-closed back end which forms an asymmetrical latch, which mates with a corresponding catch at the back of said tool collar. The sleeve has at least a flexible region (also called a living hinge) which is seated above said bearing in said guide. The flexible region of said sleeve above said bearing is displaceable by the pressure exerted thereon from the bearing moving against it as the bearing is displaced during insertion of a tool within said tool shaft. When an annular bearing guide formed in said tool aligns with said bearing, the flexible hinge moves up and down and acts to urge the bearing into the annular bearing guide. In some instances an alignment latch and catch position the sleeve in a preselected orientation whereby the flexible hinge is placed over bearing.

DRAWINGS

The above-mentioned features of the present disclosure will become more apparent with reference to the following description taken in conjunction with the accompanying drawings wherein like reference numerals denote like elements and in which:

FIG. 7B shows a perspective component view of a step down hinge body alternative (37) of the exemplary implementation of FIG. 6;

Figure 1:
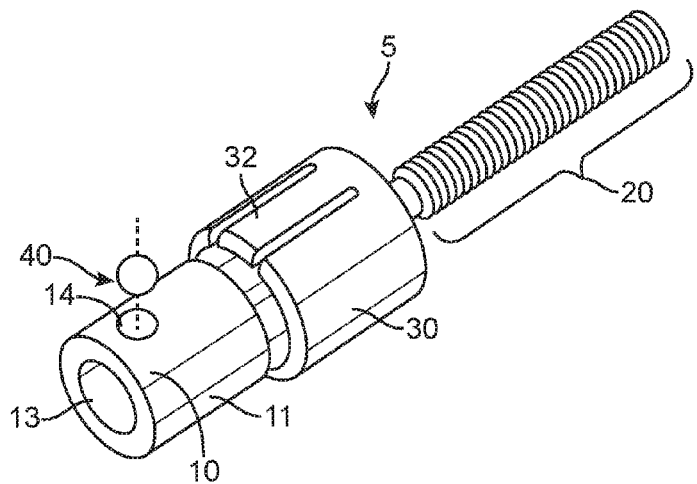
FIGS. 1 and 2 show perspective views of the assembly of flexible hinge connection of the disclosure.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

Figure 2:
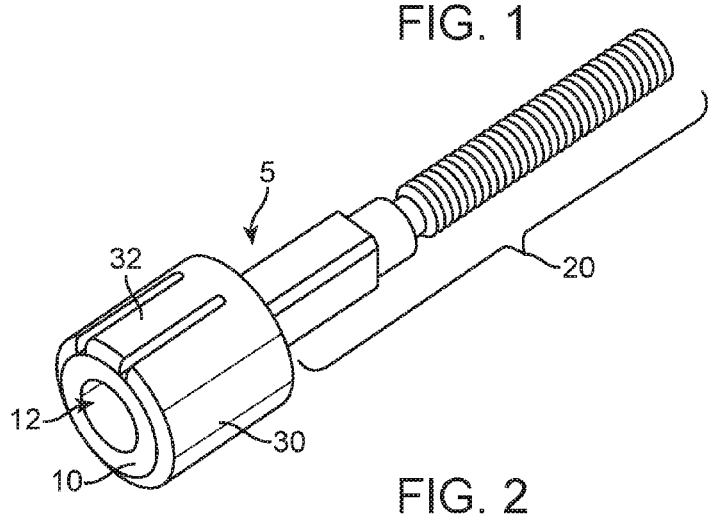
Figure 3:
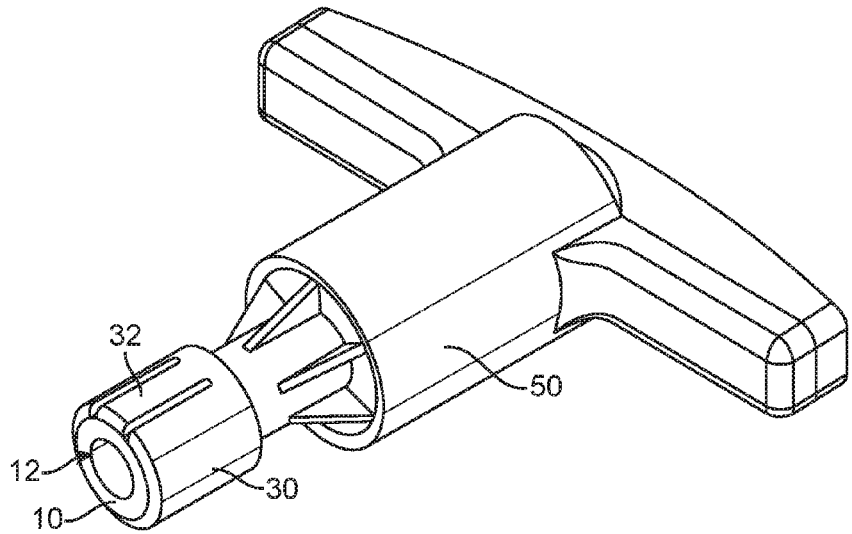
FIG. 3 shows an exemplary implementation of a tool handle with flexible tool connector of the disclosure.

According to some aspects of exemplary implementations, as shown in FIGS. 1 and 2 and 3 there is a tool mount with flexible connector 5. A tool collar 10 with a closed back end, and open front end, an outer annular wall 11 with an open ended tool socket 12 having an inner annular wall and a bearing guide 14 is shown affixed to a shaft 20. A sleeve 30 with flexible "U" hinge 32 is sized to snugly slide over the tool collar 10 and bearing guide 14. A bearing 40 fits in the bearing guide. The bearing guide 14 is an open channel with a fluid connection from the outer annular wall 11 of the tool collar 10 to the annular wall 13 of the tool socket. The edge of the bearing guide 14 also being adjacent to (and in fluid connection with) the annular wall 13 of the tool socket (which may be generally referred to as the inner wall of the tool collar) is of a diameter smaller than the diameter of the bearing 40. The edge of the bearing guide 14 adjacent to the outer annular wall 11 of the tool collar is of a diameter large enough for said bearing to move up and down within the bearing guide 14. Those of ordinary skill in the art will recognize that a tool socket may be conformed to fit a specific tool mount, geometric, radiuses, partially radiused and the like.

Figure 4:
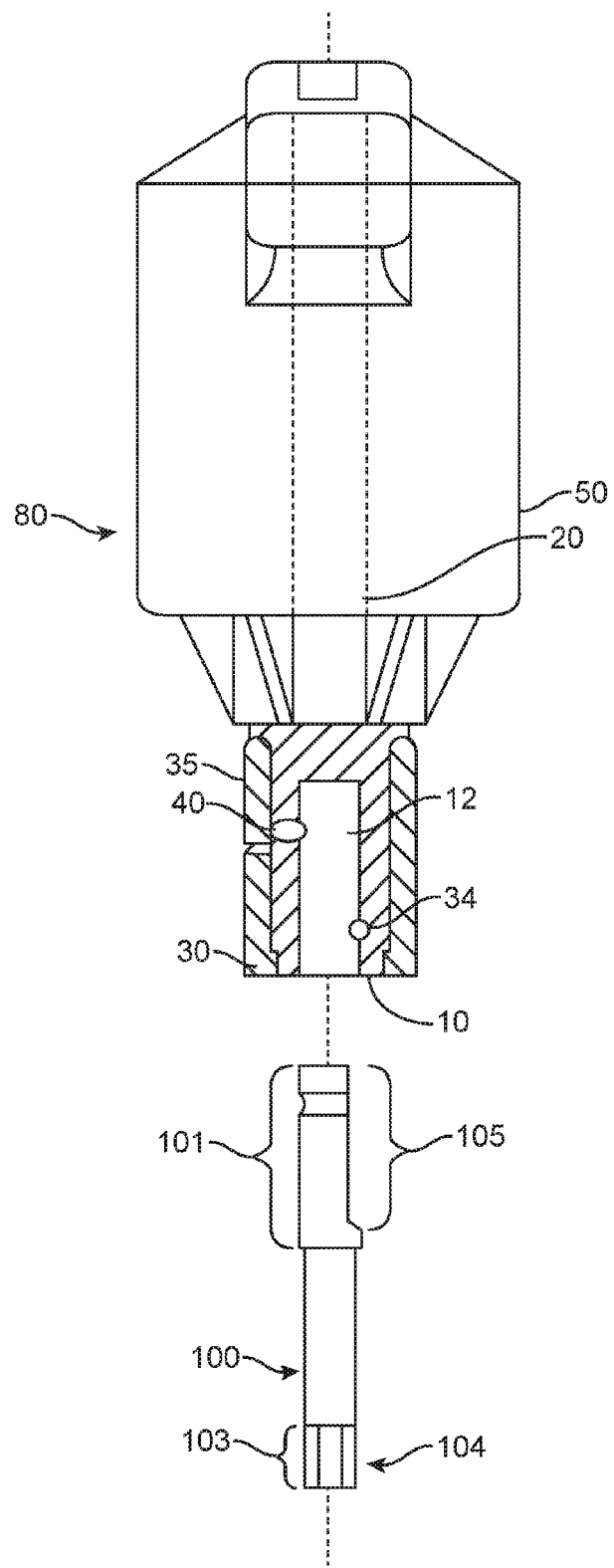
FIG. 4 shows a partial cut-away side component view of an exemplary implementation of a tool handle with flexible connection of the disclosure.
Figure 5:
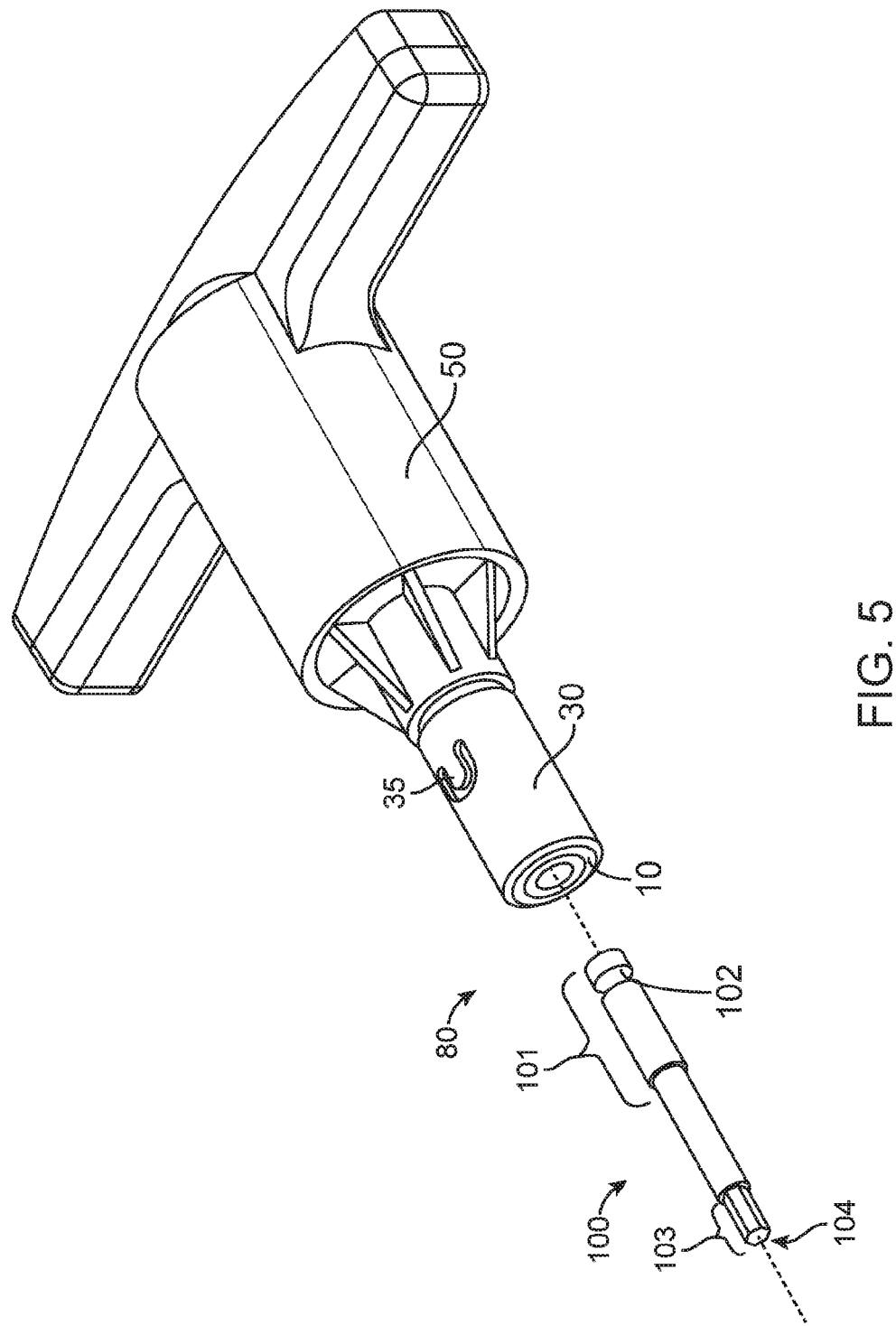
FIG. 5 shows a perspective component view of the exemplary implementation of FIG. 4.

FIGS. 4 and 5 illustrate some aspects of an exemplary implementation of a hand tool with flexible connection hinge 80. The tool collar 10 with tool socket 12 includes an alignment guide 34 which is raised within the tool socket 12. A bearing 40 in a bearing guide is movably affixed within the bearing guide and positioned beneath a flexible "C" shaped hinge body 35. The shaft 20 affixed within a handle 50 combines a tool mount with flexible connector and handle 50 forming a tool 80 (in this instances hand held) with flexible connector. Those of ordinary skill in the art will recognize that the subject matter of this disclosure is not limited to hand tools and that said shaft 20 could be designed to fit within in a collar of a powered tool and the like. Powered tools and devices include drills and other rotating devices.

A tool 100 with a shaped proximal end 101 and an annular bearing guide 102 fits within said tool socket. Said bearing is of a size and shape whereby it is displaced upward from the tool socket towards the outer wall of the tool collar constrained within said bearing guide by said flexible "C" shaped hinge body 35. Said flexible hinge being formed of an elastomeric material with memory. Materials may include, but are not limited to plastics, resins, metals, composites, rubbers and polymers. Said flexible hinge may be displaced by the force of a moving bearing. Said bearing fitting within said annular bearing guide when said flexible hinge urges said bearing therein. On the distal end 103 of the tool 100 is formed to, in some instances, provide a tool catch 104. Said tool catch may affix tools such as fastening tools, cutting tools, positioning tools and the like. The alignment guide 34 may be used to orient a tool 100 with an alignment portion 105 in the correct position. Those of ordinary skill in the art will recognize that said tool catch may be eliminated and a tool may be formed at the distal end of the tool shaft. Those of ordinary skill in the art will also recognize that such an arrangement to affix a tool shaft which may have a variety of tool catches provides a single handle which may be used with a multitude of tool platforms.

Figure 6:
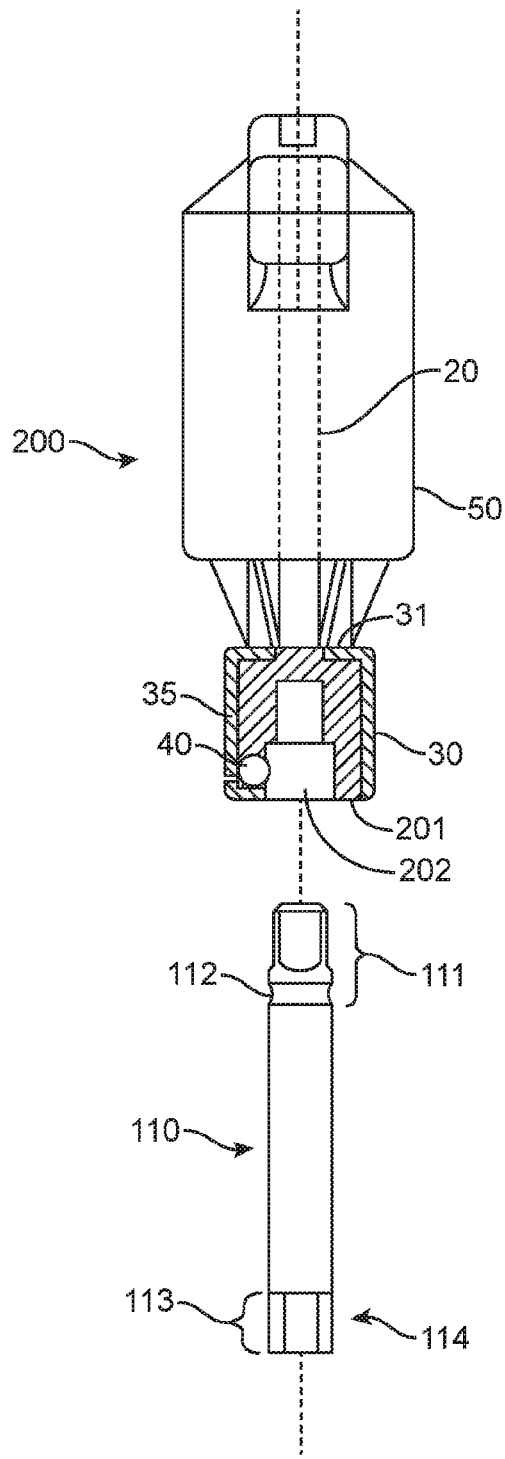
FIG. 6 shows a partial cut-away side component view of an exemplary implementation of a tool handle with flexible connection of the disclosure.
Figure 7A:
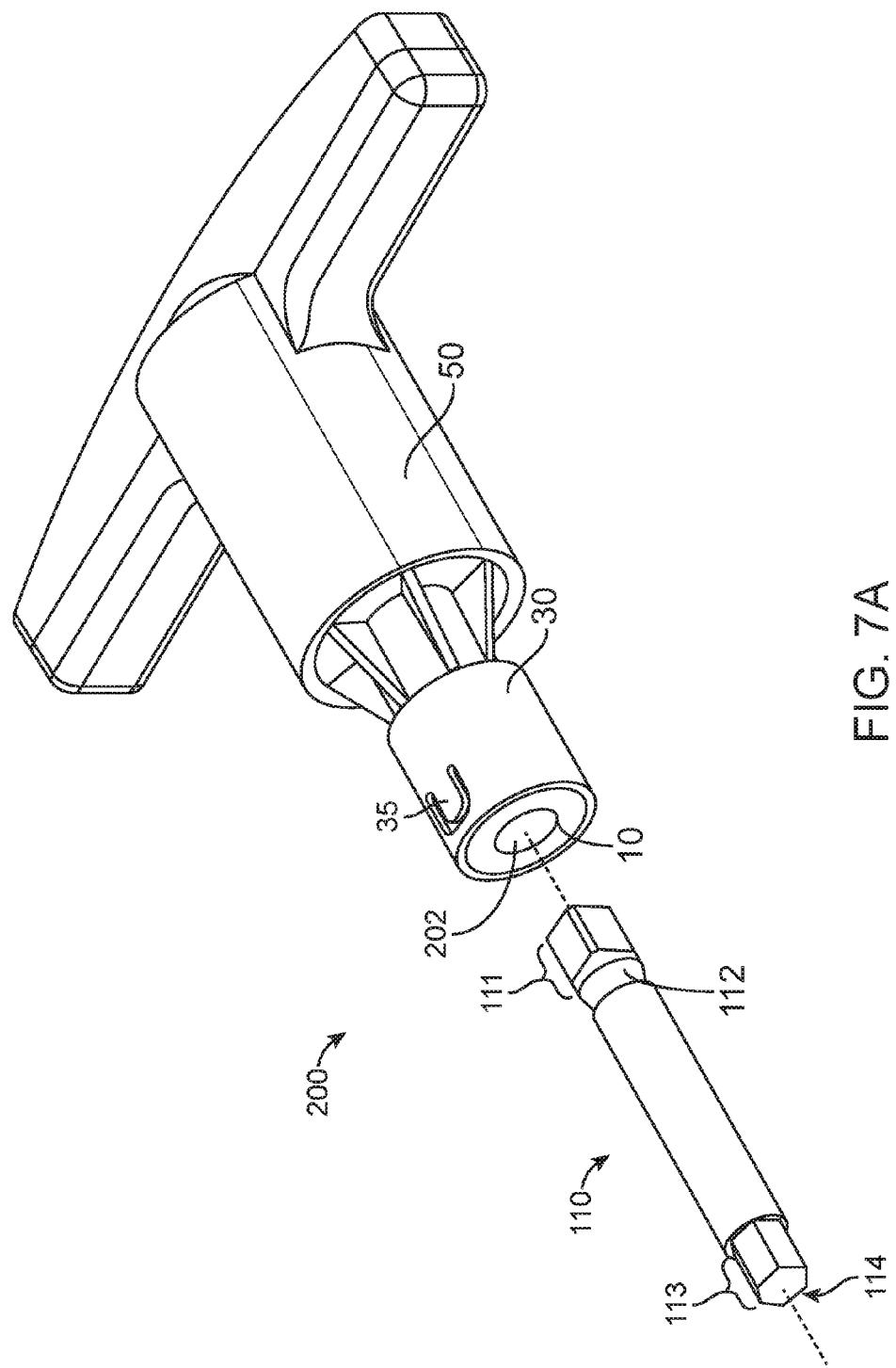
FIG. 7A shows a perspective component view of the exemplary implementation of FIG. 6.

FIGS. 6 and 7B illustrate some aspects of an exemplary implementation of a hand tool or hand device with flexible connection hinge 200. A bearing 40 in bearing guide is movably affixed within the bearing guide and positioned beneath a flexible "C" shaped hinge body 35. The shaft 20 affixed within a handle 50 combines a tool mount with flexible connector and handle 50 forming a tool 200 (in this instances hand held) with a flexible connector which fits over a tool collar 201 having a tool socket 202. A sleeve 30 with flexible "C" shaped hinge body 35 within an aperture 36 is sized to slide over the tool collar 201 and bearing and bearing guide. The sleeve 30 is generally cylindrical with a partially closed back end 31 and an open front end. FIG. 7B illustrates an alternative sleeve and hinge wherein the hinge body is a reduced thickness hinge body 37 with a first end 38 affixed to the sleeve and a free second end 39. The reduced thickness hinge body 37 is thinner than the thickness of the sleeve. Although shown as being relatively homogeneous in its thickness, the reduced thickness hinge body 37 may be tapered or otherwise non-homogeneous. The thinner hinge body reduces the force needed to insert and remove a tool 110 from the device. In medical procedures a tool may be wet, slippery or otherwise difficult to hold onto. By reducing the thickness of the hinge body less force is required to displace it.

A tool 110 with a shaped proximal end 111 and a tool latch 112 reversibly mountable to fit within a tool socket 202. The proximal end 11 displaces the bearing 40 during insertion until said bearing 40 rests in the tool latch 112 thereby acting as a catch which may also be referred to as annular. At the distal end 113 of the tool 110, in some instances, is a tool catch 114. Said tool catch may affix tools such as fastening tools, cutting tools, positioning tools and the like. Those of ordinary skill in the art will recognize that said tool catch may be eliminated and a tool may be formed at the distal end of the tool shaft. Those of ordinary skill in the art will also recognize that such an arrangement to affix a tool shaft which may have a variety of tool catches provides a single handle which may be used with a multitude of tool platforms.

Figure 8:
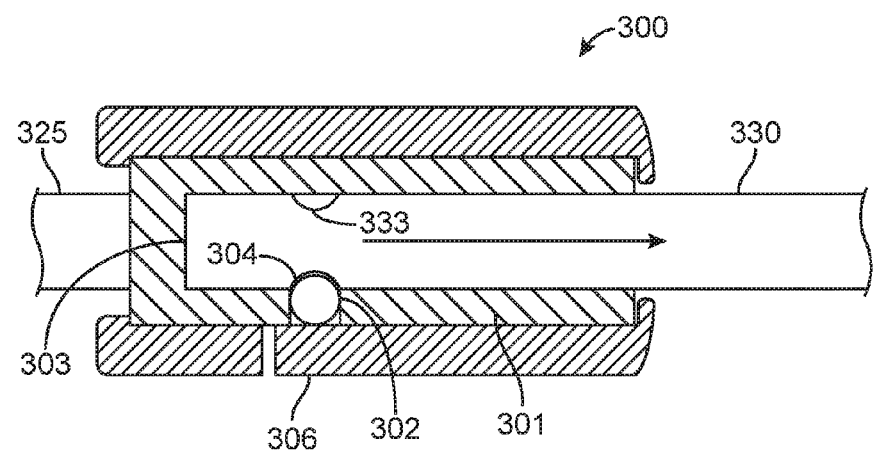
FIGS. 8 and 9 show a partial cut away view of an exemplary implementation of a tool handle with flexible tool connector of the disclosure.
Figure 9:
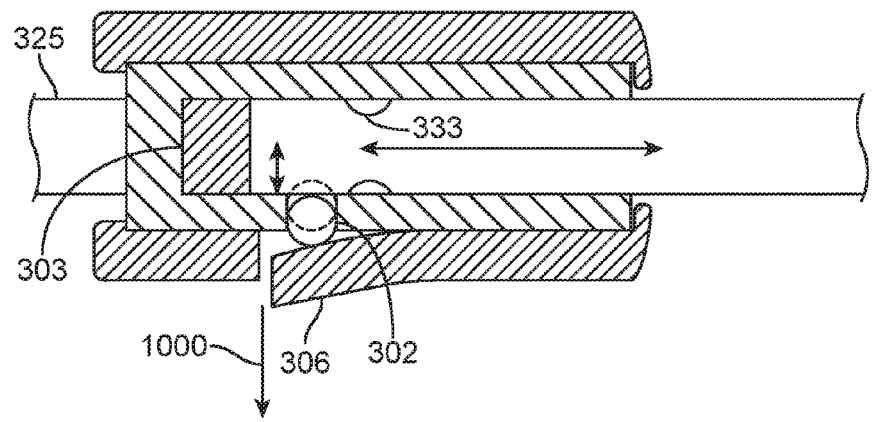

FIGS. 8 and 9 illustrate some aspects of an exemplary implementation of a hand tool or hand device with flexible connection hinge 300. The tool collar 301 with bearing guide 302 and tool socket 303. A bearing 304 in bearing guide is movably affixed within a bearing guide 302 and positioned beneath a flexible hinge 306 formed in a collar sleeve fitted over the tool collar. Although the flexible hinge 306 is illustrated as having substantially the same thickness as the sleeve, as previously described, the hinge body may be a reduced thickness hinge body to reduce the necessary force to displace same. A back shaft 325 affixed to the tool collar extends opposite the tool socket 202 and may be used to connect the tool with flexible connection hinge 300 to a handle, chuck, tool, power tool and the like. When the front tool shaft 330 is urged forward within the tool socket 303, the bearing 304 within the bearing guide 302 moves away from the tool latch 333, thereby pushing on the flexible hinge 306, thereby elastically deforming it along the line of arrow 1000 in the bearing guide 332 as front tool shaft 330 is removed from the tool socket 303.

Figure 10:
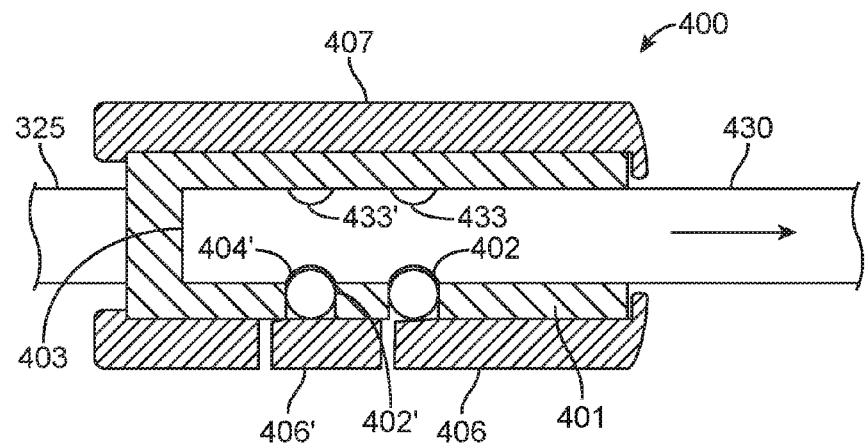
FIGS. 10 and 11 show partial cut away view of an exemplary implementation of a tool handle with flexible tool connector of the disclosure.
Figure 11:
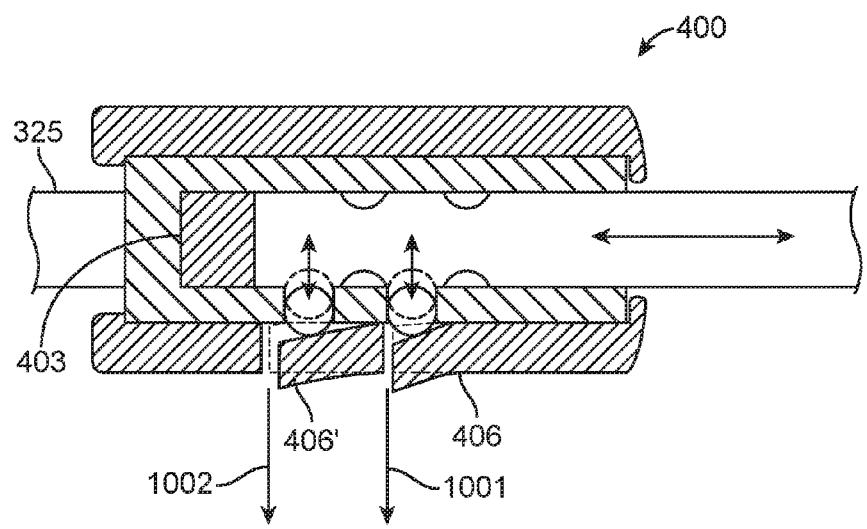

FIGS. 10 and 11 illustrate some aspects of an exemplary implementation of a tool with flexible connection hinge 400. The tool collar 401 with a first bearing guide 402 and a second bearing guide 402' and tool socket 403. A first bearing 404 is placed in the first bearing guide 402 an a second bearing 404' resides in the second bearing guide 402, each bearing being movably affixed. Both bearings are generally on the same side of the tool collar. Over the first bearing 402 is placed a first flexible hinge 406, and over the second bearing is a second flexible hinge 406' formed in a collar sleeve 407 fitted over the tool collar. Although the flexible hinge 406 and 406' are illustrated as having substantially the same thickness as the sleeve, as previously described, the hinge body may be a reduced thickness hinge body to reduce the necessary force to displace same. A back shaft 325 affixed to the tool collar extends opposite the tool socket 403 and may be used to connect the tool with flexible connection hinge 400 to a handle, chuck, tool, power tool and the like. When the front shaft 430 is urged forward within the tool socket 403, the bearing within the bearing guides (also referred to as the tool latch 433 and 433') move away from the tool socket, thereby pushing on the flexible hinges, elastically deforming said flexible hinges along the line of arrows 1001 and 1002.

Figure 12:
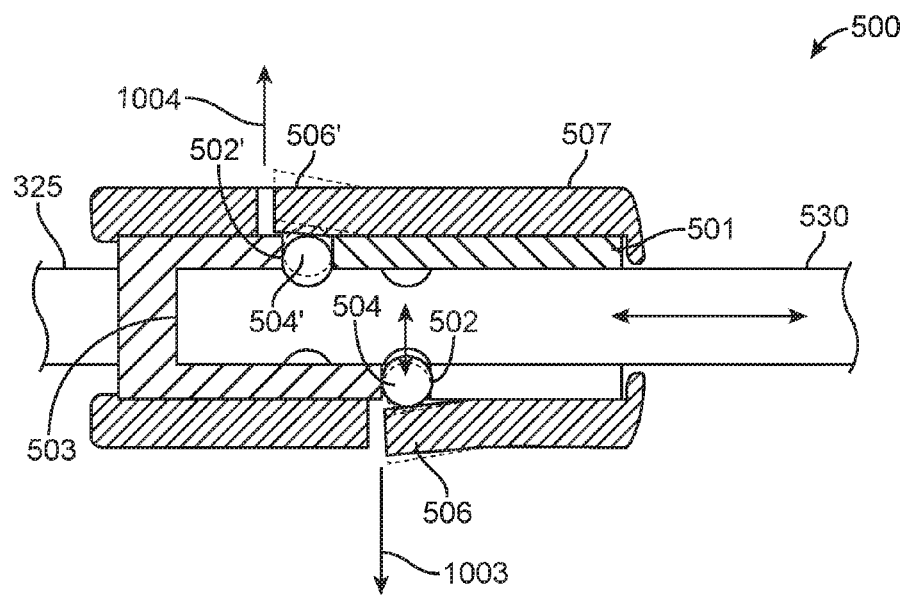
FIG. 12 shows a partial cut away view of an exemplary implementation of a tool handle with flexible tool connector of the disclosure.

FIG. 12 illustrates some aspects of an exemplary implementation of a hand tool or hand device with flexible connection hinge 500. The tool collar 501 with a first bearing guide 502 and a second bearing guide 502' and tool socket 503 is shown. A first bearing 504 is placed in the first bearing guide 502 and a second bearing 504 resides in the second bearing guide 504, each bearing being movably affixed. Both bearings are dis-aligned on the tool collar. Over the first bearing 502 is placed a first flexible hinge 506, and over the second bearing 504 is a second flexible hinge 506', formed in a collar sleeve 507 fitted over the tool collar. A back shaft 325 affixed to the tool collar extends opposite the tool socket 503 and may be used to connect the tool with flexible connection hinge 500 to a handle, chuck, tool, power tool and the like. If the front shaft 530 is urged forward within the tool socket 503, the bearing within the bearing guides 525 will move away from the tool socket pushing on the flexible hinges, and will thereby elastically deform it along the line of arrows 1003 and 1004 as front shaft 530 is removed from the tool socket 503. Although the flexible hinges 506 and 506' are illustrated as having substantially the same thickness as the sleeve, as previously described, the hinge body may be a reduced thickness hinge body to reduce the necessary force to displace same.

Figure 13:
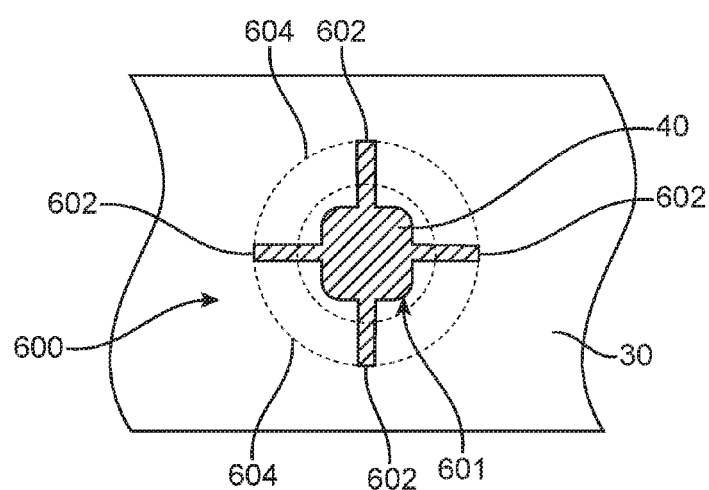
FIG. 13 shows a partial cut away view of an exemplary implementation of a sleeve with flexible hinge of the disclosure.

FIG. 13 shows a top view of a flexible hinge 600. A sleeve 30 has a circular ball alignment 601 formed therein. A plurality of channels 602 extend from said ball alignment. A ball bearing 40 is held beneath said ball alignment in a bearing guide (not shown). The ball alignment 601 has a diameter smaller than that of said ball bearing. Flexible flaps 604 are formed between each pair of channels. Said flaps have multiple free edges at the ball alignment, and at the channels. The portion of the flap attached to the larger sleeve (between said channels) forms a natural hinge, and when said ball bearing pushes upward at the ball alignment said flap yields and is displaced to allow movement. By utilizing material with memory, the flaps will urge the ball bearing back into the bearing guide and to mate with any catch or latch on a tool that said bearing may temporarily affix. Although the flexible flaps 604 are illustrated as having substantially the same thickness as the sleeve the flap may be a reduced thickness flap to reduce the necessary force to displace same.

Figure 14A:
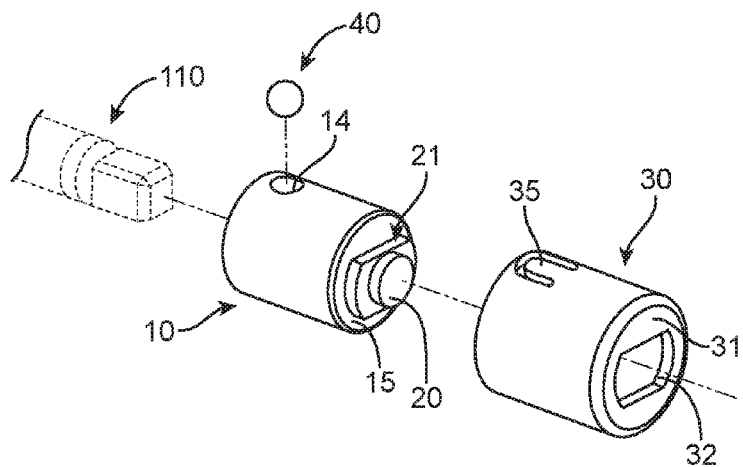
FIG. 14A shows a partial assembly view of components of a flexible tool connector.
Figure 14B:
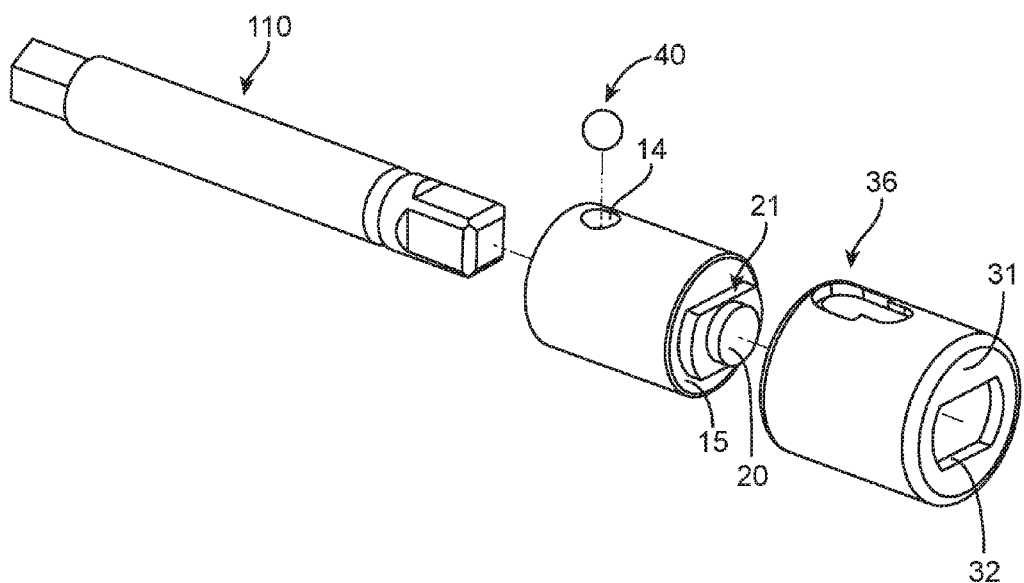
FIG. 14B shows show perspective views of the assembly of reduced thickness flexible hinge connection of the disclosure.
Figure 15:
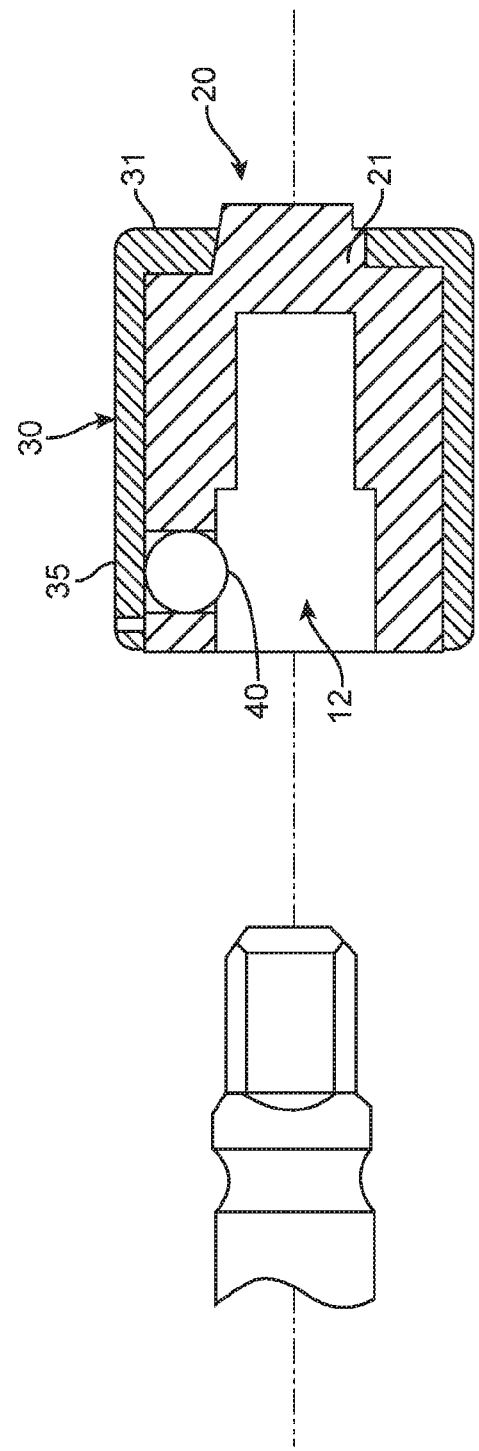
FIG. 15 shows a cut-away view of a flexible tool connection and a tool end of FIG. 14A.

According to some aspects of exemplary implementations, as shown in FIGS. 14A and 15, there is a tool mount with flexible connector. A tool collar 10 with a closed back end 15 and open front end forming tool socket 12 having an inner annular wall and a bearing guide 14 is shown affixed to a portion of a shaft 20. For illustration purposes, shaft 20 is not fully shown. A sleeve 30 with flexible "U" shaped hinge body 35 is sized to snugly slide over the tool collar 10 and bearing guide 14. A bearing 40 fits in the bearing guide. The bearing guide 14 is an open channel with a fluid connection from the outer annular wall of the tool collar 10 to the annular wall of the tool socket. The interface of the shaft with the back end 15 of the tool collar 10 has an asymmetrical extension from the back of the tool collar and/or around the shaft which is a positioning catch 21. FIG. 14B shows an alternative sleeve and hinge wherein the hinge body is a reduced thickness hinge body 37. The thinner hinge body reduces the force needed to insert and remove a tool 110 from the device. In medical procedures, a tool may be wet, slippery or otherwise difficult to hold onto. By reducing the thickness of the hinge body, less force is required to displace it.

Figure 16:
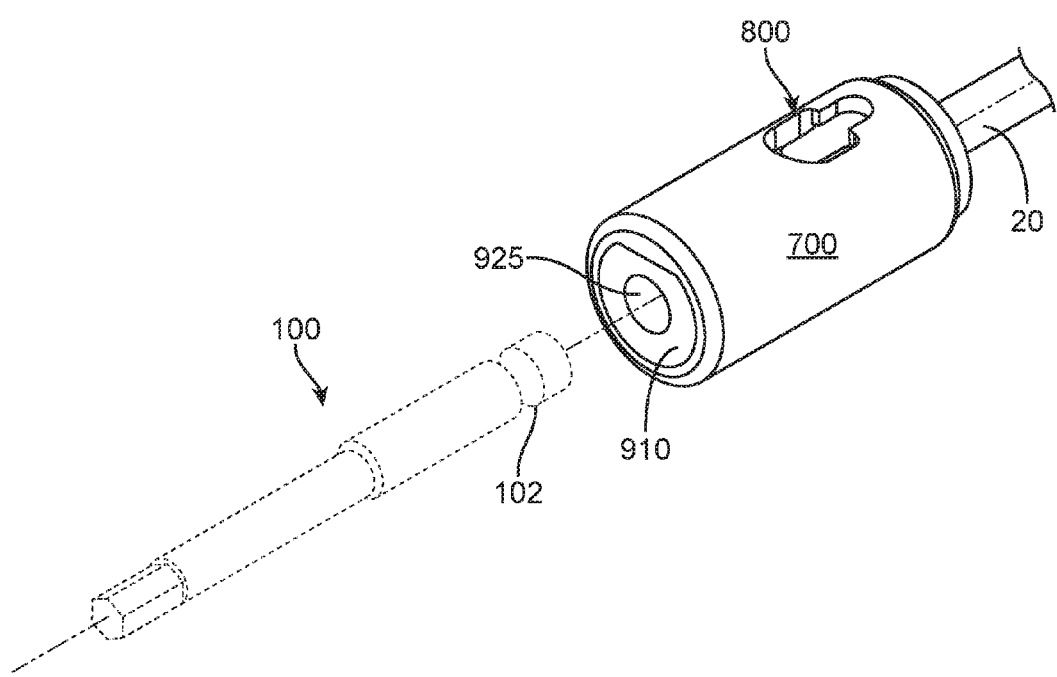
FIG. 16 shows a perspective view of a front aligned flexible tool connector.
Figure 17:
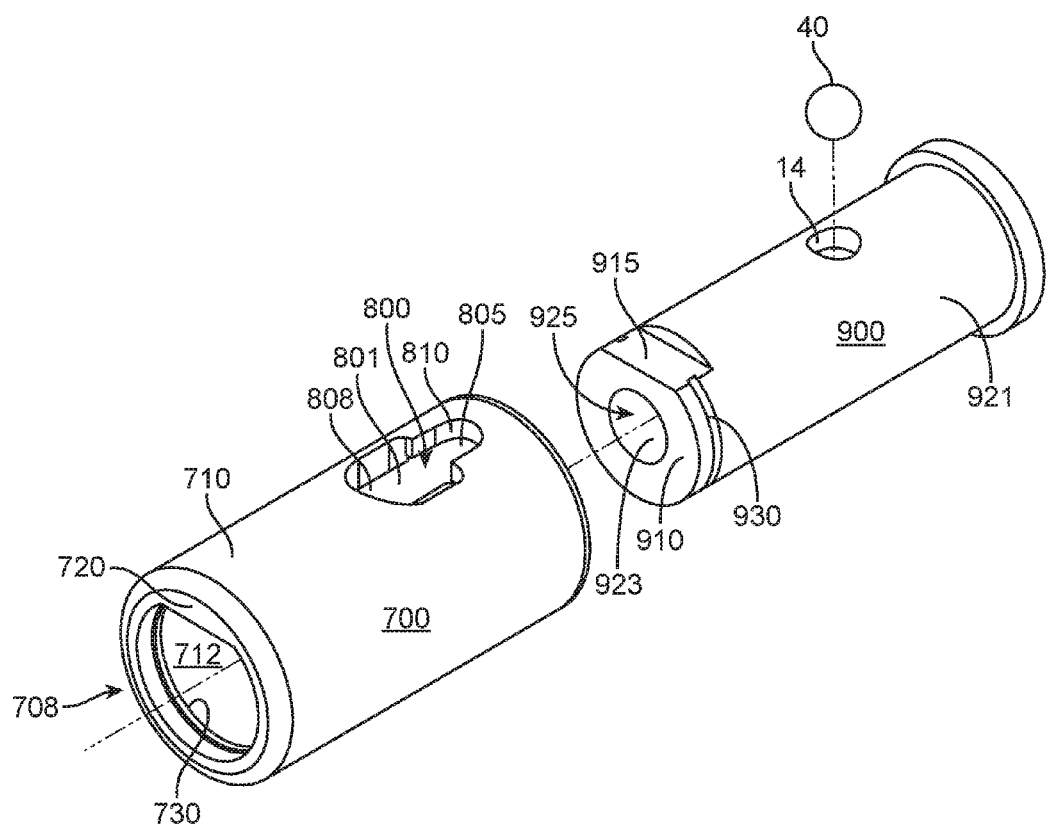
FIG. 17 shows a component view of a front aligned flexible tool connector.

FIGS. 16 and 17 show an assembled and a component view of a front aligned sleeve with flexible hinge. Although FIGS. 16 and 17 show the flexible hinge as a reduced thickness hinge body 800, those of ordinary skill in the art will recognize that the alignment disclosed herein is not limited to a reduced thickness hinge body and is equally applicable to the hinge body 35 described above.

Figure 18:
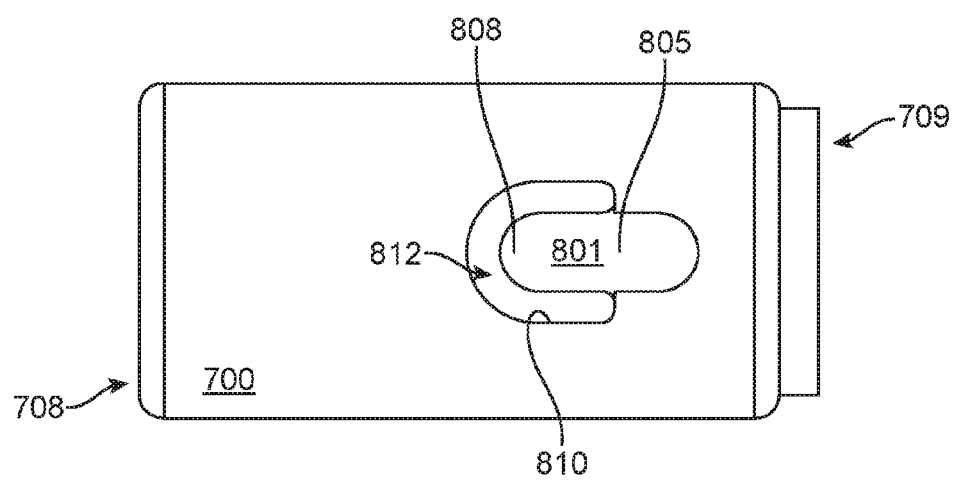
FIG. 18 is a top view of a reduced thickness flap formed in a sleeve.

FIGS. 16, 17 and 18 illustrate an exemplary implementation of a front aligned flexible hinge device with a reduced thickness hinge body 800. A shaft 20 is connected to the back of the tool collar 900. The front of the tool collar 910 is generally ovoid or circular with a non-homogeneous portion 915, in this instance shown as a non-radiused section, acts as a positioning/alignment catch. That non-homogeneous section may be a groove, rib, concavity or other catch. A bearing guide 14 is an open channel with a fluid connection from the outer annular wall 921 of the tool collar 900 to the annular wall 923 of the tool socket 925. The edge of the bearing guide 14 also being adjacent to (and in fluid connection with) the annular wall 925 of the tool socket (which may be generally referred to as the inner wall of the tool collar) is of a diameter smaller than the diameter of the bearing 40. The edge of the bearing guide 14 adjacent to the outer annular wall 921 of the tool collar is large enough for said bearing to move up and down within the guide.

The sleeve 700 is generally cylindrical with an open back end 705, a partially-open front end 708, an open back end 709, an outer annular wall 710, an inner annular wall 712, and an alignment latch 720. The flexible hinge flap 801 is constructed of a material with memory, which, when at rest is generally aligned with the inner annular wall. The flap 801 is flexible at its connected first end 805, and when displaced, it moves out of alignment with the inner annular wall, thereby opening up the bearing guide 14 to allow movement of the bearing 40 within the guide. When assembled, the sleeve 700 slips over the tool collar 900. The positioning guide is an asymmetrical alignment latch 720 mating with the alignment catch 915 limiting assembly to one orientation, and thereby preventing rotation of the sleeve 700 around the tool collar 900. Those of ordinary skill in the art will recognize that a positioning catch/latch cooperative arrangement may be reversed, wherein the latch is on the sleeve and the catch on the tool collar, or vice versa.

In some instances and implementations, an internal rib 730 circumnavigates a portion of the inner annular wall 712 of the sleeve. The rib 730 acts as a latch with a grove formed in the tool collar's outer annular wall 921. The rib mates with the grove 930 to hold the sleeve in place upon the tool collar.

The sleeve has the reduced thickness hinge body 800 formed therein. The flap 801 is thinner than the surrounding sleeve material, and has an attached first end 805 and a free second end 808. The attached first end is affixed to or formed as part of the flap guide 810, which is a well or depression which may be sloped or orthogonal to the flap. The second end 808 of the flap 801 is separated from the flap guide 810 by a channel 812, which allows the second end 808 to move without rubbing or binding against the sides of the well that is the reduced thickness flap guide shown.

Figure 19:
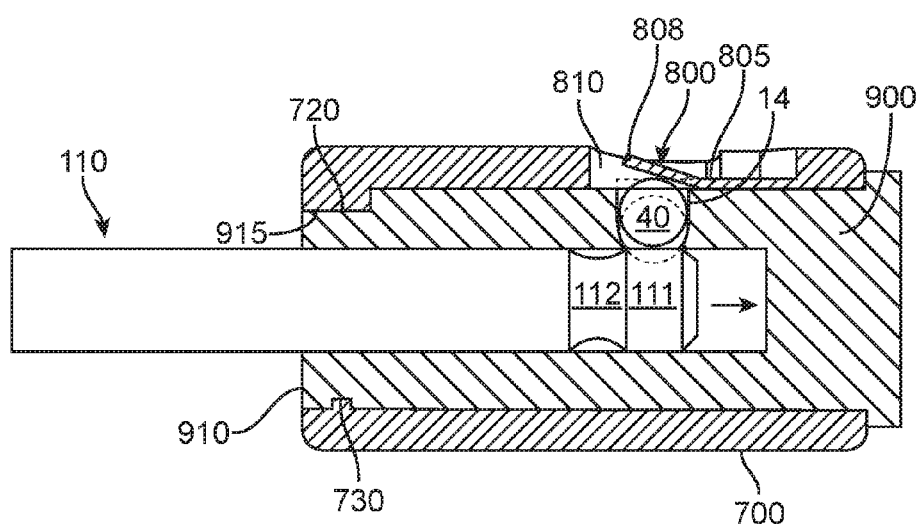
FIGS. 19 and 20 are sequential cut away views of the insertion and catching of a tool shaft inserted via a reduced thickness hinge.
Figure 20:
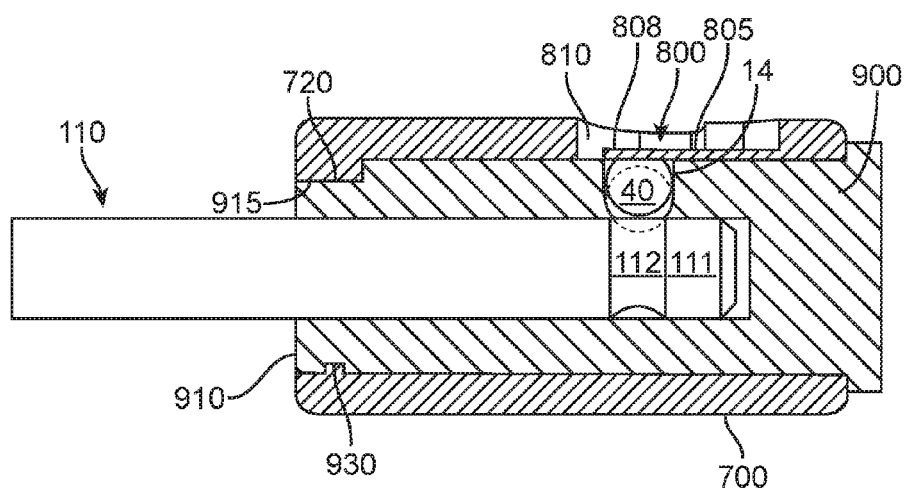

FIGS. 19 and 20 are sequenced views of a method of reversibly connecting a tool 110 with a shaped proximal end 111 and a tool latch 112 into a tool collar 900, reversibly mountable to fit within a tool socket 925. When the shaped proximal end 111 encounters the bearing 40 during insertion, by applying adequate force to displace the free second end 808 of the reduced thickness hinge body 800, the bearing 40 moves away from the tool socket, thereby allowing the shaped proximal end 111 to pass through. When the tool is fully inserted (FIG. 20), the tool latch (which is an annular groove around the tool) aligns with the bearing guide 14 and the flexible reduced thickness hinge body 800, which is connected to the flap guide 810 via the first end 805, returns to its at rest position, thereby holding the bearing 40 in the tool latch 112.

With the bearing guide flap 800, the sleeve slips over the tool collar with the alignment latch 720, mating with the alignment catch 915, which orients the flap 801 over the bearing 40. In some instances, a rib 730 is utilized. The rib will mate with a groove 930 to hold the sleeve onto the tool collar. The proximal end 111 displaces the bearing 40 during insertion into the tool socket 925, until said bearing 40 rests in the tool latch 112, thereby acting as a catch.

A sleeve 30 with flexible "C" shaped hinge body 35 is sized to snugly slide over the tool collar 10 and bearing guide. The sleeve 30 is generally cylindrical with a partially closed back end 31 and an open front end. Formed through the partially closed back end 31 is an asymmetrical latch 32 which receives the positioning catch 21 which forms an alignment guide. The latch and catch are utilized to position the hinge body 35 in a preselected orientation to the bearing 40. Those of ordinary skill in the art will recognize that said positioning latch catch may be chosen from a plethora of shapes which all would be within the present disclosure.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

It should be noted that the bearings may be adjusted to correspond to the intended usage. A highly lubricous material may be used, a ball shape, cone, cylinder or ovoid.

The invention claimed is:

1. A tool mount with flexible connector comprising:
   a tool collar (201) with a closed back end (15) and an open front (12) and an outer annular wall and an open ended tool socket having an inner annular wall;
   a bearing guide (14) with a fluid connection from the outer annular wall (11) to the inner annular wall (13);
   a bearing fitted within said bearing guide;
   a generally cylindrical sleeve (30) with an outer annular wall (710) and inner annular wall (712) having an open end (708) and a partially closed end (709);
   said sleeve fitted over the tool collar;
   a reduced thickness flexible hinge (37) formed in the sleeve, fluidly connecting the outer and inner annular walls; and,
   a shaft (325) attached to the closed back end of the tool collar.

2. The tool mount with flexible connector of claim 1, wherein said flexible hinge is one of "U" shaped (32) and "C" (35) shaped.

3. The tool mount with flexible connector of claim 1, wherein the diameter of the bearing guide near the inner annular wall is of a smaller diameter of said bearing.

4. The tool mount with flexible connector of claim 1, further comprising an alignment positioning catch (21) on the tool collar.

5. The tool mount of claim 4, wherein an alignment guide is one of a latch and a catch.

6. The tool mount of claim 5, wherein the alignment positioning catch further comprises:
   a partially closed latch (32) at the back end of the sleeve;
   a positioning catch (21) formed at the dosed back end of the tool collar; and, whereby the latch and catch mate in a preselected orientation.

7. The tool mount of claim 5, wherein the alignment guide further comprises:
   a partially closed latch (720) at the front end of the sleeve;

a non-homogeneous portion (915) of the tool collar outer annular wall proximate to the front end forming a catch; and, whereby the latch and catch mate in a preselected orientation.

8. The tool mount with flexible connector of claim 7, further comprising a tool catch (114) at the distal end (114) of said tool.

9. The tool mount with flexible connector of claim 7, wherein said sleeve has memory and is formed of at least one of plastics, resins, metals, composites, rubbers, and polymers.

10. The tool mount with flexible connector of claim 1, further comprising a tool (100) with a shaped proximal end (111) and an annular bearing guide (112) reversibly mountable to said tool socket.

11. A hand held device comprising:
a tool collar with a closed back end and an open front and an outer annular wall and an open ended tool socket having an inner annular wall;
a bearing guide with a fluid connection from the outer annular wall to the inner annular wall;
a bearing fitted within said bearing guide;
a shaft extending from said closed back end;
a positioning catch formed on at least one of the open front end and the back end of the tool collar; and,
a sleeve with an open front end and a partially closed back end having a latch which mates with said positioning catch over the tool collar with a flexible hinge formed therein.

12. The device of claim 11, wherein an alignment further comprises:
a partially closed latch (32) at the back end (31) of the sleeve;
a positioning catch (21) formed at the closed back end of the tool collar; and, whereby the latch and catch mate in a preselected orientation.

13. The device of claim 11, wherein an alignment guide further comprises:
a partially closed latch (720) at the front end of the sleeve; and,
a non-homogeneous portion (915) of the tool collar outer annular wall proximate to the front end forming a catch.

14. The device of claim 11, wherein said flexible hinge is a reduced thickness (801)
compared to the sleeve.

15. The device of claim 11, further comprising:
a groove (930) formed in a tool collars annular wall (921);
a rib (730) formed inside a sleeve inner annular wall (712);
and, whereby the rib mates with the groove.

16. A method of reversibly attaching tools, the method comprising:
surrounding a tool collar having a tool socket therein with a cylindrical sleeve having and open front end, a partially open back end and a flexible hinge, fluidly connecting the outer and inner walls of the sleeve;
mating an orientation of the flexible hinge in the sleeve around the tool socket with a first asymmetrical alignment guide on the back end of the sleeve to a second guide on the back end of the tool collar whereby the hinge is positioned over a bearing; inserting a tool shaft with shaped proximal end and tool guide formed therein, into the tool socket; and,
using force to move the bearing with the proximal end of the tool whereby the bearing moves away from the tool socket against the flexible hinge and causes the flexible hinge flap to become displaced and allow passage of the tool shaft.

17. The method of claim 16, further comprising further inserting the tool shaft until the bearing moves into the tool socket and mates with the tool guide.

18. The method of claim 16, further comprising keeping the position of the flexible hinge over the bearing in a preselected orientation via the first and second guides.

19. A method of reversibly attaching tools, the method comprising:
surrounding a tool collar having a tool socket therein with a cylindrical sleeve having and open front end a partially open back end and a flexible hinge, fluidly connecting an outer and inner walls of the sleeve;
mating an orientation of the flexible hinge in the sleeve around the tool socket with a first asymmetrical alignment guide on the front end of the sleeve to a second guide on the front end of the tool collar whereby the hinge is positioned over a bearing;
inserting a tool shaft with shaped proximal end and tool guide formed herein, into the tool socket; and,
using force to move the bearing with the proximal end of the tool whereby the bearing moves away from the tool socket against a flexible hinge and causes the flexible hinge flap to become displaced and allow passage of the tool shaft.

20. The method of claim 19, the method further comprising further inserting a tool shaft until the bearing moves into the tool socket and mates with the tool guide.

21. The method of claim 19, the method further comprising keeping the position of a flexible hinge over the bearing in a preselected orientation via the first and second guides.

\* \* \* \* \*